United States Patent [19]

Kidwell et al.

[11] Patent Number: 5,637,508

[45] Date of Patent: *Jun. 10, 1997

[54] BIOMOLECULES BOUND TO POLYMER OR COPOLYMER COATED CATALYTIC INORGANIC PARTICLES, IMMUNOASSAYS USING THE SAME AND KITS CONTAINING THE SAME

[75] Inventors: David A. Kidwell, Alexandria, Va.; Susan M. Conyers, Kalamazoo, Mich.

[73] Assignees: Geo-Centers, Inc., Newton Centre, Mass.; The United States of America as represented by the Secretary of the Navy, Washington, D.C.

[ * ] Notice: The term of this patent shall not extend beyond the expiration date of Pat. No. 5,384,265.

[21] Appl. No.: 376,396

[22] Filed: Jan. 23, 1995

Related U.S. Application Data

[63] Continuation-in-part of Ser. No. 37,981, Mar. 26, 1993, Pat. No. 5,384,265.

[51] Int. Cl.$^6$ .................... G01N 33/551; G01N 33/553
[52] U.S. Cl. ................... 436/525; 435/75; 435/28; 435/975; 436/37; 436/66; 436/84; 436/172; 436/501; 436/518; 436/524; 436/543; 436/544; 436/805; 436/808
[58] Field of Search .................. 435/28, 7.5, 975; 436/37, 66, 84, 172, 501, 518, 524, 525, 543, 544, 546, 805, 808

[56] References Cited

U.S. PATENT DOCUMENTS

| | | | |
|---|---|---|---|
| 4,313,734 | 2/1982 | Leuvering | 436/525 |
| 4,496,658 | 1/1985 | Kondo et al. | |
| 4,503,143 | 3/1985 | Gerber et al. | |
| 4,663,278 | 5/1987 | DiNello et al. | |
| 5,128,476 | 7/1992 | Zhang et al. | |
| 5,384,265 | 1/1995 | Kidwell et al. | 436/525 |

OTHER PUBLICATIONS

Rideal, "Catalytic Hydrogenation with Protected Hydrosols", pp. 749–756, (1920).
Pilipenko et al, *Journal of Analytical Chemistry USSR*, vol. 28, pp. 1004–1008, (1971).
Larpent et al, *Journal of Molecular Catalysts*, vol. 65, pp. L35–L40, (1991).
Lucocq et al, *Techniques in Immunocytochemistry*, vol. 3, pp. 204–236 (1985).
Frens, *Nature Physical Science*, vol. 241, pp. 20–22 (1973).
Horisberger, *Scanning Electron Microscopy*, pp. 19–40 (1981).
Ismail et al, *Biosens Bioelectronics*, vol. 6, pp. 698–705 (1991) (Abstract).
Martin et al, *J. Immunoassay*, vol. 11, pp. 31–48 (1990) (Abstract).
Tijssen, *Practice and Theory of Enzyme Immunoassays*, Elsevier, NY, pp. 175–178 (1985).
Filippov et al, *J. of Anal. Chem. USSR*, vol. 19, pp. 441–443 (1964).
Rigin et al, *J. of Anal. Chem. USSR*, vol. 30, pp. 2028–2031 (1975).
Babko et al, *Ukr. Khim. Zh.*, vol. 35(2), pp. 194–199 (1969) (Abstract).
Groh et al, *Z. Phys. Chem.*, vol. 88 pp. 414–418 (1914).
De Gregario Roscasolano, *Comptes Rendus*, vol. 173, pp. 234–236, (1921), Abstract attached *Chem. Abstracts*, vol. 15, p. 3018 (1921).
Pauli et al, "Der Aufbau der Platin–Sole", *Kolloid Zeitschrift* I (1935).
Gillet, *Mikrochimica Acta* [Wien], II, pp. 467–477 (1977).
Albrecht, *Z. physikal. Chem* . . . , vol. 136, p. 321 (1928) (Abstract).
Bielstein Pt[A]–68, pp. 391–430.
Lukovskaya et al, Catalytic action of iridium and platinum in the chemiluminescence reaction between luminol and hydrogen peroxide, *Zh. Anal. Khim.*, vol. 33. pp. 750–753, (1978); CA89(12):99086(e).

*Primary Examiner*—Christopher L. Chin
*Attorney, Agent, or Firm*—Oblon, Spivak, McClelland, Maier & Neustadt, P.C.

[57] ABSTRACT

Polymer or copolymer coated catalytic colloidal metal particles bound to a biomolecule such as an antibody, avidin, or streptavidin and kits containing such polymer or copolymer coated catalytic metal particles are useful for detecting the presence of the biomolecule in an assay such as an immunoassay.

18 Claims, 3 Drawing Sheets

BIOMOLECULES BOUND TO POLYMER OR COPOLYMER COATED CATALYTIC INORGANIC PARTICLES, IMMUNOASSAYS USING THE SAME AND KITS CONTAINING THE SAME

This application is a CIP of U.S. Ser. No. 08/037,981 filed Mar. 26, 1993 and issued as U.S. Pat. No. 5,384,265 on Jan. 24, 1995. U.S. Ser. No. 08/037,981 is incorporated herein by reference.

BACKGROUND OF THE INVENTION

1. Field of the Invention

The present invention relates to biomolecules which are bound to catalytic inorganic particles, immunoassays which utilize such biomolecules, and kits for carrying out such immunoassays.

2. Discussion of the Background

The detection of trace amounts of biologically significant compounds, such as steroids or drugs of abuse, is often accomplished quickly and inexpensively by the employment of an immunoassay. Such an assay relies on an immunogenic recognition of the substance in question followed by the amplification of that recognition. Enzymes are widely used in immunoassays as the amplifier of the antibody-antigen recognition event. One of the most common types of immunoassays is the Enzyme-Linked Immunosorbant Assay (ELISA).

ELISA may be preformed in a number of different ways. The two most common are the competitive mode and the sandwich assay. In a competitive mode ELISA, a surface, usually either a polystyrene plate or a nitrocellulose membrane, is coated with a capture antigen. These surfaces are normally chosen because they bind protein non-specifically. Therefore, if the antigen is not a protein, it may be covalently linked to a carrier protein and bound to the surface without further chemistry. After the antigen is bound, the remaining binding sites on the surface are blocked with another protein. Then the test fluid and enzyme-labeled antibody are added. If no antigen is in the test fluid, all the labeled antibody will bind to the antigen adsorbed on the surface. Conversely, if antigen is present in the test fluid, the antigen will block the binding sites on the enzyme-labeled antibody and prevent it from binding to the antigen adsorbed on the surface. The surface is washed to remove unbound materials, and a substrate is added for the enzyme. The enzyme catalyzes a reaction in which the substrate reacts to form a colored material which can be quantitatively observed with a spectrophotometer. The intensity of the color produced is proportional to the enzyme activity and the amount of antibody bound, which is inversely proportional to the amount of antigen in the test fluid.

In a sandwich assay ELISA, an antibody that recognizes part of the antigen is bound to a surface. Since antibodies are proteins, this is readily accomplished by allowing the surface to contact a solution of the antibody. As in the competitive ELISA, the remaining sites on the surface are blocked with another protein. The test fluid is then added. If an antigen is present in the test fluid, the antibody on the surface will capture the antigen. Then a second, enzyme-labeled antibody, which recognizes a different part of the antigen than the first antibody, is added. The second antibody will then bind to the antigen which is captured on the surface. After washing the surface to remove any unbound materials, a substrate for the enzyme is added and the color produced is observed spectrophotometrically. In this form of an ELISA, the signal is directly proportional to the concentration of the antigen in a test sample. Such a sandwich assay is widely used in the commercial arena for home pregnancy tests.

In either type of ELISA, the enzyme acts as the amplifier of the antigen-antibody reaction. That is, a color or other signal, such as light from some chemiluminescent reaction, is produced that can be observed macroscopically. Without this amplification step, the sensitivity of an immunoassay would be orders of magnitude less.

Several problems occur in the use of enzymes as amplifiers in immunoassays. They are:

1. Any change in enzyme activity will affect the precision of the assay. For example, loss of half of the activity of the enzyme in a competitive ELISA may produce a false positive since less signal indicates the presence of the test substance. Since enzyme activity is sensitive to storage conditions, enzymes must be kept either refrigerated, freeze dried or both. Also, controls must be performed to constantly test the activity of the enzyme. Inevitably, the shelf-life is limited by the stability of the enzyme.

2. Enzymes are expensive. Being derived from living sources, they require substantial processing costs. The least expensive enzyme, on an activity basis, is Horseradish Peroxidase which is not surprisingly the most common enzyme used in ELISAs. However, even Horseradish Peroxidase costs about $5/mg or $5000/g, a cost which is about 450 times the cost of gold. Fortunately, very little enzyme is necessary for each assay.

3. The labeling of antibodies with enzymes is often a quite laborious procedure as one must ensure that little unbound enzyme is present. If significant amounts of unbound enzyme are present or significant amounts of unlabeled antibody are present, the sensitivity of the ELISA is reduced.

4. Enzymes are often heterogeneous materials due to their isolation from natural sources. Therefore, characterization of enzyme-antibody conjugates can be difficult.

Enzymes are also used for detection of the hybridization of DNA or RNA to its complimentary strand, often in conjunction with amplification of the DNA or RNA target by the polymerase chain reaction (PCR). These reactions are widely employed for DNA fingerprinting, and the detection of genetic defects, viruses and bacteria. Because the PCR reaction requires heating and cooling of the reaction mixture to cause denaturation of the DNA, the common enzymes such as peroxidase or alkaline phosphatase cannot be added to the reaction mixture until after the amplification reactions occur. This limits some of the procedures that can be preformed. Catalytic particles do not have this limitation and therefore give more flexibility to the detection of nucleic acids.

Colloidal metals have been employed in immunoassays previously. Mostly, they consisted of either colloidal iron or gold (M. Horisberger, "Colloidal Gold: A Cytochemical Marker for Light and Fluorescent Microscopy and for Transmission and Scanning Electron Microscopy", *Scanning Electron Microscopy*, pp. 19–40 (1981); and Martin et al, "Characterization of Antibody Labelled Colloidal Gold Particles and Their Applicability in a sol Particle Immunoassay, SPIA", *J. Immunoassay*, vol. 11, pp. 31–48 (1990)). However, in either case, the metals were only chosen for their color, i.e., their presence is determined only by their color or electron density under an electron microscope. Both the color and electron density are directly proportional to the mass of the metal colloid, not their catalytic activity. Thus a relatively large amount of material is necessary to be observed and they can only compete in sensitivity to enzyme-type amplifiers of the antibody-antigen reaction when the signal is further amplified by an instrument such as an electron microscope.

Similarly, the use of colloidal gold and colloidal silver as markers in histochemistry has also been reported. (Lucocq and Roth, "Colloidal Gold and Colloidal Silver-Metallic Markers for Light Microscopic Histochemistry", *Techniques in Immunochemistry*, vol. 3, pp. 203–236 (1985)). Again, the colloidal particles were not detected on the basis of any catalytic activity. More recently amplification of gold colloids has occurred via a process very similar to photography. The gold colloids act as nucleation sites for the precipitation of silver, which is the colormetric material (see p. 273 of the 1993 BioRad Life Sciences Research Product Catalog, Hercules, Calif.).

Stable colloidal rhodium (0) suspensions have been reported to catalyze the hydrogenation of liquid alkenes in biphasic systems under mild conditions (Larpent et al, "New Highly Water-Soluble Surfactants Stabilize Colloidal Rhodium (0) suspensions Useful in Biphasic Catalysts", *J. Molecular Catalysis*, vol. 65, pp. L35–L40 (1991)). However, there is no report of such colloidal rhodium particles being bound to a biomolecule, such as an antigen.

The oxidation of luminol (5-amino-2,3-dihydro-1,4-phthalazinedione) by hydrogen peroxide is a chemiluminescent reaction known to be catalyzed by colloidal platinum (Albrecht, *Z. Phys. Chem.*, vol. 136, p. 321 (1928)). However, there is no report of such colloidal platinum being bound to a biomolecule.

Tris(2,2'-bipyridine)ruthenium II has been used as a peroxide-producing replacement for an enzyme label (Ismail and Weber, "Tris-2,2'-Bipyridineruthenium-II as a Peroxide-Producing Replacement for Enzymes as Chemical Labels", *Biosens. Bioelectronics*, vol. 6, pp. 698–705 (1991). However, the hydrogen peroxide is produced by photolysis with such compounds, and accordingly, the use of such labels in an assay requires the use of photolysis equipment.

SUMMARY OF THE INVENTION

Accordingly, it is an object of the present invention to provide novel compounds which can be used for the immunoassay of an analyte which do not suffer from the above-described drawbacks.

It is another object of the present invention to provide compounds in which a biomolecule is bound to a catalytically active moiety which is stable on long-term storage.

It is another object of the present invention to provide compounds in which a biomolecule is bound to a catalytically active moiety which is stable at elevated temperatures.

It is another object of the present invention to provide compounds which are catalytically active at conditions at which biomolecules are stable and which are easily accessible.

It is another object of the present invention to provide compounds which are catalytically active at room temperature, near neutral pH, and in aqueous media.

It is another object of the present invention to provide a novel immunoassay utilizing a compound in which a biomolecule is bound to a catalytically active moiety which is stable on long-term storage.

It is another object of the present invention to provide a novel immunoassay utilizing a compound in which a molecule is bound to a catalytically active moiety which is stable at elevated temperatures.

It is another object of the present invention to provide novel kits for carrying out such immunoassays.

These and other objects, which will become apparent during the following detailed description, have been achieved by the inventor's discovery that a catalytic particle based on a metal colloid possesses catalytic activity equivalent to that of an enzyme. Unlike enzymes, metals do not lose activity over time and no special handling is necessary. Since metals are readily obtained from their ores, even precious metals, such as platinum, cost about $12/g or 400 times less than the typically used enzymes. Some catalytic particles will adsorb antibodies and other proteins nonspecifically which makes attachment easy. In some preparations, the catalytic particles are significantly larger than the antibodies or proteins or more dense. Therefore, the particles may be separated from unbound antibody by any number of physical techniques such as size exclusion chromatography or centrifugation.

This disclosure describes the preparation of colloidal metal catalytic particles for the replacement of enzyme amplification of molecular recognition, their labeling with proteins, their purification, their use in immunoassays, and kits for carrying out such immunoassays.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
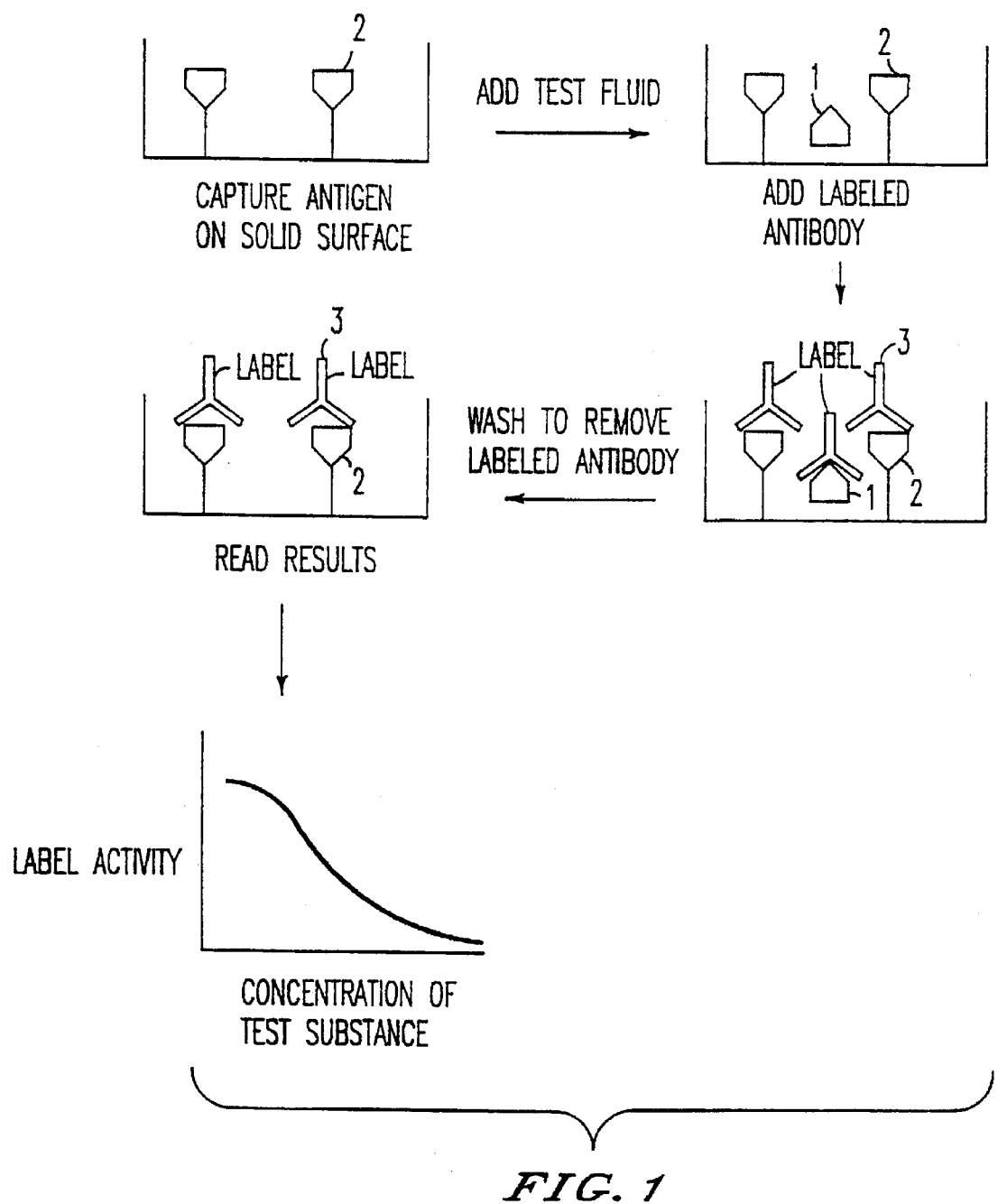
FIG. 1 schematically illustrates a competitive mode assay according to the present invention.

Thus, in a first embodiment, the present invention relates to novel compounds in which a biomolecule is bound to a catalytically active colloidal metal particle. The criteria for selection of the colloidal metal is that a colloid of the metal should be easily prepared, the colloid should be capable of being labeled with a protein, the colloid should not coagulate while in solution, and the colloid should be capable of catalyzing a colorimetric or chemiluminescent reaction. Accordingly, the colloidal metal particle may suitably comprise any metal which is catalytically active as a colloidal particle and meets those criteria. Preferably, the metal is any transition metal. Particularly preferred metals are Ni, Fe, Ag, Pt, or Pd. Most preferably, the metal is Pt. Alloys of one or more catalytically active metals with one or more other catalytically active metals or with one or more inert metals may be used, including platinum-gold alloys, platinum-iron alloys, any alloy containing at least one of the above-described metals, etc.

It should be understood that the colloidal metal particle may comprise more than one metal. Thus, the colloidal metal particle may comprise two or more metals which are catalytically active as a colloidal particle, e.g., a colloidal particle of Pt and Pd. Alternatively, the colloidal metal particle may comprise an inactive or inert metal, such as gold, in addition to the catalytically active metal.

In the context of the present invention, the term "catalytically active" means the ability to catalyze any reaction which may conveniently used as the signal amplification in an immunoassay. Examples of such reactions include:

1. The transfer of hydrogen from hydrogen donors (HD) to $H_2O_2$:

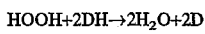

HOOH+2DH→2H₂O+2D

D=hydrazine, 1,2-dihydroxybenzene, diakyl-N,N' phenylenediamine, 1,3-dihydroxybenzene, 1,4-dihydroxybenzene, 1,2,3-trihydroxybenzene, σ-phenylenediamine, σ-methoxyphenol, coniferol, leucomalachite green, benzidine, ascorbic acid, guaiacol, diaminobenzidine, 5-aminosalicylic acid, σ-dianisidine, the diammonium salt of 2,2'-azino-di-(3-ethyl-benzthiazoline sulfonate-6), 3-methyl-2-benzothiazolinone hydrazone, 3-(dimethylamino) benzoic acid, and σ-tolidine.

Platinum and palladium are widely used as catalysts in organic chemistry. Since these particles stay in aqueous solution, there is the opportunity to use these materials in that solvent. Aqueous solutions offer advantages in cost of the solvent and disposal of the waste. Several systems have been studied in the past for the use of colloidal platinum in organic reactions (c.f. *Gemelin Handbuch fur Anorganischen Chemie*, Platin A3, pp. 429–430). However, with the discovery of Adam's catalysis, experimentation with colloids appears to have been discontinued.

Suitably, the colloidal metal particle is small enough that agglutination will not occur and the colloidal particles will remain in the aqueous phase for times as long as weeks or months. Although the upper size limit will depend, in part, on the storage conditions and identity of the metal, it has been found for Pt that good results are achieved if the colloidal particles are smaller than 50 nm in their greatest dimension, preferably less than 10 nm in their greatest dimension. Suitably, the colloidal particles have a smallest dimension of at least about 1 to 5 nm.

In addition, the invention colloidal metal particle may be partially or wholly coated with any polymer or copolymer. Polymers and copolymers having any number average molecular weight may be used. Preferred are those with number average molecular weights of from about 800 to about 3 million, including those with number average molecular weights of 100,000, 500,000, 1,000,000, 2,000,000 and 2,500,000. Particularly preferred are block or graft copolymers that contain both anchoring groups and stabilizing chains like those described in Ross, S. and Morrison, I., *Colloidal Systems and Interfaces*, Wiley, N.Y., 1988, incorporated herein by reference in its entirety. See page 357 for preferred materials. The amount of polymer or copolymer preferably ranges from 0.01% to 1500% based on the weight of the invention metal colloid particle, but any amount can be used. Mixtures of polymers, mixtures of copolymers, and mixtures of polymers and copolymers can be used. Further, preferred polymers and copolymers are water-soluble polymers including those listed in Ross, S. and Morrison, I., *Colloidal Systems and Interfaces*, Wiley, N.Y., 1988, Molynenx, P. *Water-Soluble Synthetic Polymers: Properties and Behavior*, vols. I and II, , CRC Press, Inc., Boca Raton, Fla., 1983, and those vinyl polymers, particularly polyvinyl alcohols, described in the *Kirk-Othmer Encyclopedia of Chemical Technology*, vol. 23, p. 798ff, Wiley & Sons, New York 1983, all of which are incorporated herein by reference in their entireties. Among preferred polymer and copolymer materials, in addition to the polyvinyl alcohols described above, are polyethylene oxides, polyethylene glycols, poly(acrylic acid), poly (ethylene imine), poly(methacrylic acid), poly(phosphoric acid), poly(styrene sulfonic acid), polyvinyl amine, poly(4-vinylbenzoic acid), and salts thereof, particularly alkali metal salts and alkaline earth metal salts. In addition, those polymers and copolymers listed in the *Polymer Handbook*, J. Brandrup and E. Immergut, Eds., Wiley & Sons, New York 1989, those generically described in the *Index of Polymer Trade Names*, 2nd, greatly enlarged edition, VCH, Weinheim 1992, and those in *Polymers in Aqueous Media*, Advances in Chemistry Series 223, ACS, Washington, D.C., 1989, all of which are incorporated herein by reference in their entireties, may be used. Likewise the polymers and copolymers may be combined with other linkers, such as in Carbowax 20M (a poly(ethylene glycol) compound with 2,2'-[(1-methylethylidene) bis (4,1-phenyleneoxymethylene)] bis oxirane).

The colloid metal particles may be prepared by any conventional method. A number of methods for producing colloidal particles which are suitable for the present invention have already been reported, and these are described below.

A number of reducing agents for gold are known and include citrate (G. Frens, "Controlled Nucleation for the Regulation of the Particle Size in Monodisperse Gold Suspensions", *Nature Physical Science*, vol. 241, pp. 20–22 (1973)), formate, ascorbate, formaldehyde, phosphorus, ethanol, and tannic acid (M. Horisberger, "Colloidal Gold: A Cytochemical Marker for Light and Fluorescent Microscpy and for Transmission and Scanning Electron Microscopy", *Scanning Electron Microscopy*, pp. 19–40 (1981)). Less work has been done on platinum. Gutbier (A. Gutbier, "Inorganic Colloids", *Z. Chem Ind. Kolloide*, vol. 5, pp. 46–52 and 105–109) prepared a colloidal platinum and palladium solution with hydrazine, but no catalytic reactions were reported.

Brintzinger reduced a number of metals with ascorbic acid and related materials (H. Brintzinger, "Ascorbic and Isoascorbic Acids as Reducing Media in the Formation of Colloid Disperse Solutions of Gold, Palladium, Platinum, Silver, Selenium, Tellurium, Molybdenum Blue and Tungsten Blue", *Kolloid-Z.*, vol. 78, pp 22–23 (1937); c.f. Chemical Abstracts, vol. 31 (1937)). Fillippov and Gushchina have employed formic acid/sodium formate (M. P. Filippov and L. F. Guschcina, "Determination of Colloidal Platinum by a Kinetic Method", *Journal of Analytical Chemistry USSR*, vol. 19, pp. 441–443 (1964)) to form colloidal platinum and determined the platinum concentration by its catalytic effect on the reduction of phosphomolybdenum blue at pH 2.7.

Gillet also reduced platinum with formate and determined its presence by the catalytic reduction of methylene blue in acid media (C. Gillet, Jr., "Separation, par Amalgamation en Mileiu Homogene, et Dosage Catalymetrique du Platine avec le Systeme or-Formiate-Bleu de Methylene", *Mikrochimica Acta* [*Wien*], II, pp. 467–477 (1977)). Pilipenko and Terletskaya prepared colloidal platinum and palladium and determined that they produced chemiluminescence with lucigenin (A. T. Pilipenko and A. V. Terletskaya, "Catalytic Effect of the Platinum Metals in Their Colloidal State on the Reaction Between Lucigenin, Hydrazine, and Oxygen", *Journal of Analytical Chemistry USSR*, vol. 28, pp. 1004–1008 (1971)). In no case were these particles attached to biomolecules or employed in immunoassays, and in most cases the reaction conditions employed are quite severe. All of the references cited in this and the preceding paragraphs describing the production of colloidal metal particles are incorporated herein by reference.

Some of the classical reducing agents produce colloidal particles that are too large for immunoassays or coagulate during formation. Thus, a large series of buffers and reducing conditions were tested as in Example 1. Some of the conditions and results are shown in Table 1.

The colloidal metal particle is most conveniently bound to the biomolecule by physical adsorption. Typically, the colloidal particle in a medium comprising phosphate buffer at a pH near the isoelectric point of the biomolecule is incubated with the biomolecule. The incubation is typically carried out at room temperature for a time of 5 minutes to several days, preferably about 1 hour. The colloidal metal to biomolecule ratio is adjusted by a number of factors. The products are run by electrophoresis on an agarose gel, and the shift in mobility noted when the colloidal metal is bound to the biomolecule. Alternatively, immunoassays are run with the product and the concentration of the biomolecule is chosen to produce maximum sensitivity. The metal particles will aggregate if the biomolecule is not coated sufficiently on the surface. This aggregation takes several hours to days at room temperature. However, it may be accelerated by centrifugation of the colloids at 50,000 Gs for 1 hour. The pellet that results will easily resuspend if the colloidal particles are sufficiently coated with the biomolecule. This may serve as a third method to determine the optimum ratio of biomolecule/colloid.

For example, good results have been achieved by the following process. A preparation of colloidal Pt particles is prepared by adding 50 µl of an 8 wt. % solution of platinum chloride in water (prepared from $H_2PtCl_6$, Pt content~4 wt. %) to 10 ml of $H_2O$ in which has been dissolved 300 mg of ascorbic acid and 300 mg of $NaHCO_3$. The resulting mixture is heated to near boiling until it turns brown (about 30 min) and then cooled to room temperature. 100 µl of the resulting colloidal suspension is added to about 100 µl of buffer and then 1 to 10 µg of protein is added to achieve a final protein concentration of 5 µg/ml to 50 µg/ml, and the mixture is incubated for about 1 hour.

Within the context of the present invention, the term biomolecule refers to any molecule which can be used in an immunological assay. Specifically, biomolecules which may be used in the present invention included antibodies (monoclonal and polyclonal), avidin, and streptavidin, proteins, proteins with a hapten attached, or antigens.

It should also be understood that the colloidal metal particle may be bound to a biomolecule which is not a polypeptide via a molecule which is a polypeptide. Thus, a colloidal metal particle may be adsorbed on, e.g., avidin which can in turn be bound to biotin, which in turn may be covalently bound to, e.g., a polynucleic acid or a polyribonucleic acid. Further, the biomolecule of the present invention can be attached through adsorption, absorption or via a covalent bond to the invention polymer/copolymer ((co) polymer) coated-colloidal metal particle. The biomolecule can be attached to the (co)polymer itself, to the metal particle itself, or to both. Thioether, ether, ester, urea, etc., linkages may be used for the covalent bonding. Any bond-forming synthetic methodology that produces a covalent bond directly between the biomolecule and the colloidal metal particle or between the biomolecule and the polymer or copolymer coating can be used. In addition, linker molecules like polypeptides may be used, as well as covalent bonds formed with carbodiimides, etc.

The covalent bond between the biomolecule and the colloidal metal particle may be to a metal or alloy contained therein, and the biomolecule may be preferentially bonded to one metal where more than one metal is present therein. Where the particle is wholly or partially coated with polymer and/or copolymer the biomolecule is adsorbed, absorbed or covalently bonded to either or both the metal or polymeric material. For example, in a colloidal metal particle comprising a polyvinyl alcohol (pva)-coated platinum/gold alloy colloidal metal particle, the biomolecule may be preferentially covalently bound to one or more of pva molecules, platinum atoms or gold atoms. In such an alloy, the gold is coupled to platinum through intermixing in the alloy.

The present biomolecules bonded to a catalytically active colloidal metal particle may be used directly after preparation and while in an aqueous suspension. Alternatively, the biomolecule bonded to the colloidal particle may be stored in the form of an aqueous solution for varying periods of time before being used. In another embodiment, the biomolecule bonded to the colloidal particle is stored as a dry powder, which may be obtained, e.g., by lyophilization.

The present biomolecules which are bound to a colloidal metal particle may be used in a number of different types of immunoassays. The present biomolecules are particularly useful as replacements for the enzyme-linked biomolecules currently used in ELISAs.

ELISAs are discussed in detail in Tijssen, *Practice and Theory of Enzyme Immunoassays*, Elsevier, N.Y., (1985), which is incorporated herein by reference. ELISAs are also discussed in Engvall et al, *Immunochemistry*, vol. 8, p. 871 (1971); Engvall et al, *Methods in Enzymology*, vol. 70 (1980); U.S. Pat. Nos. 4,558,012; 5,176,999; 5,173,404; Reissue Pat. No. 31,006; and Reissue Pat. No. 32,696; all of which are incorporated by reference. Enzymes which are used in activity amplification assays include peroxidase, β-galactosidase, alkaline phosphatase, urease, glucose oxidase, glucoamylase, carbonic anhydrase, and acetylcholinesterase. As noted above, Horseradish peroxidase is the most widely used enzyme in ELISAs.

FIG. 1 schematically illustrates a competitive mode ELISA utilizing an antibody labelled with a colloidal metal particle. A test fluid, which may contain the target antigen (1), is added to a container which contains immobilized target antigen (2). Then antibody (3) which binds to the target antigen and which is labelled with a colloidal metal particle is added. After incubation and washing, the amount of label remaining in the container is measured. A higher amount of antigen in the test sample will result in a lower amount of label detected.

Figure 2:
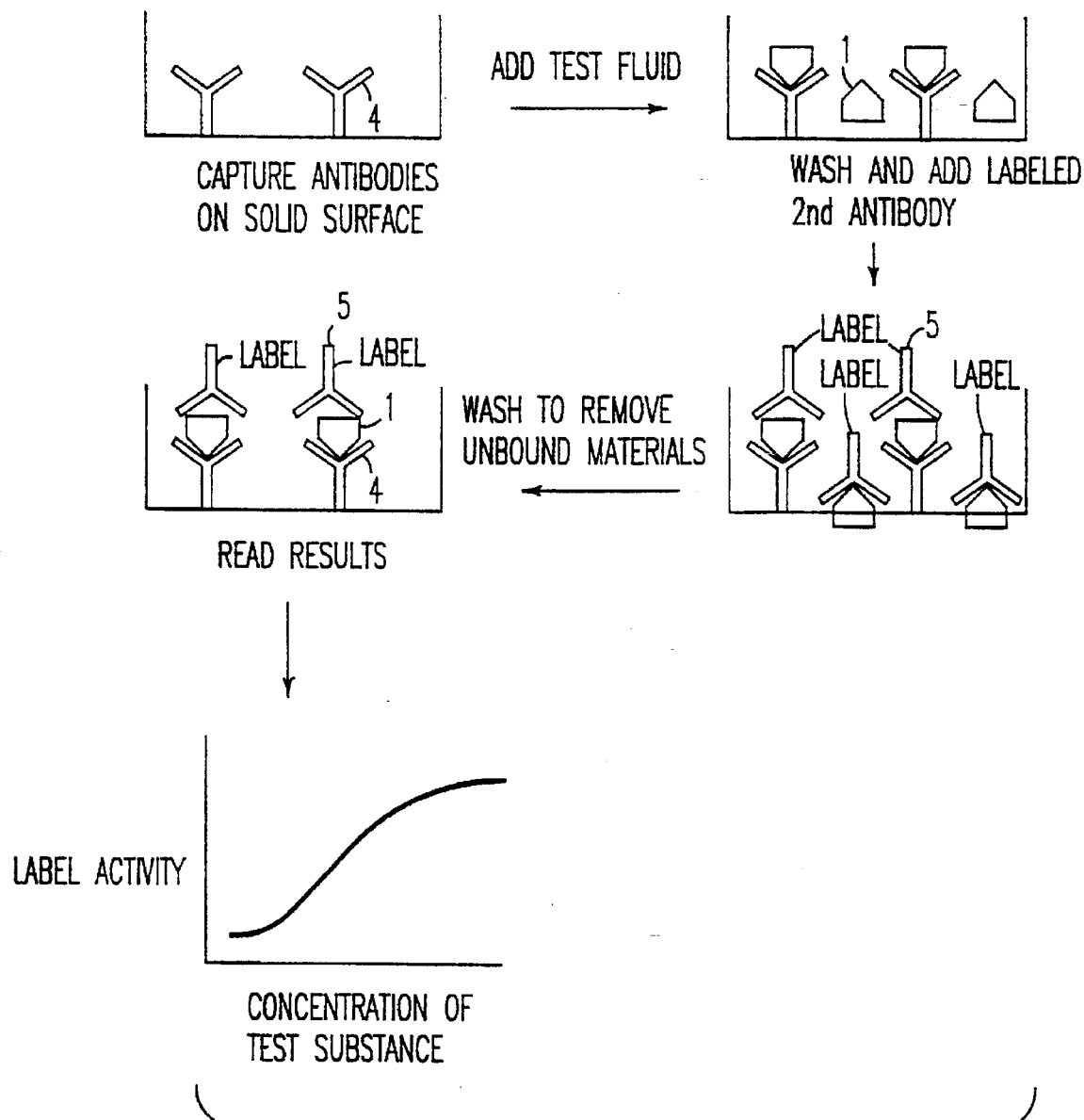
FIG. 2, schematically illustrates a sandwich mode assay according to the present invention.

FIG. 2 schematically illustrates a sandwich mode ELISA, according to the present invention. A test sample which may contain the target antigen (1) is added to a container which contains immobilized antibody (4) specific for a first epitope on the target antigen. Then antibody (5) which is labelled with a colloidal metal particle and recognizes a second epitope of the target antigen is added. After incubation and washing, the amount of label remaining in the container is measured. A higher amount of antigen in the test sample will result in a higher amount of label detected.

It will be readily recognized by those of skill in the art that these methods are also useful for the detection of antibodies in a test sample as well as antigens in test sample.

Although the above-described ELISAs are many times useful for obtaining quantitative results, it is often sufficient that the test provide only qualitative results. In particular, qualitative results are sufficient for a home or early pregnancy test.

In a preferred embodiment, the biomolecule will be streptavidin. Typically, the colloidal particle bound to streptavidin will be used in conjunction with an antibody or antigen which is covalently linked to biotin. The labelling of antibodies and antigens with biotin is well within the abilities of the skilled artisan. Preferably, the colloidal particle bound to streptavidin is used in conjunction with an antibody bound to biotin. In this way, it is possible to tailor the present assay for the detection of any desired antigen by judicious choice of the antibody bound to biotin.

The present biomolecules bound to a colloidal metal particle are also useful for determining the presence or absence of a specific sequence of RNA or DNA. The present molecules are particularly useful for detecting the presence of a target DNA in conjunction with the polymerase chain reaction.

In a first type of DNA or RNA assay, a sequence of DNA or RNA which is complementary to the target DNA or RNA is immobilized on a support, and the immobilized DNA or RNA is treated first with the test sample which may contain the target DNA or RNA and then with a sequence of DNA or RNA which is labelled with a colloidal metal particle and which will also hybridize with the initially immobilized DNA or RNA. After incubation and washing, the amount of label is measured. This embodiment is essentially the same as the competitive ELISA described above.

Figure 3:
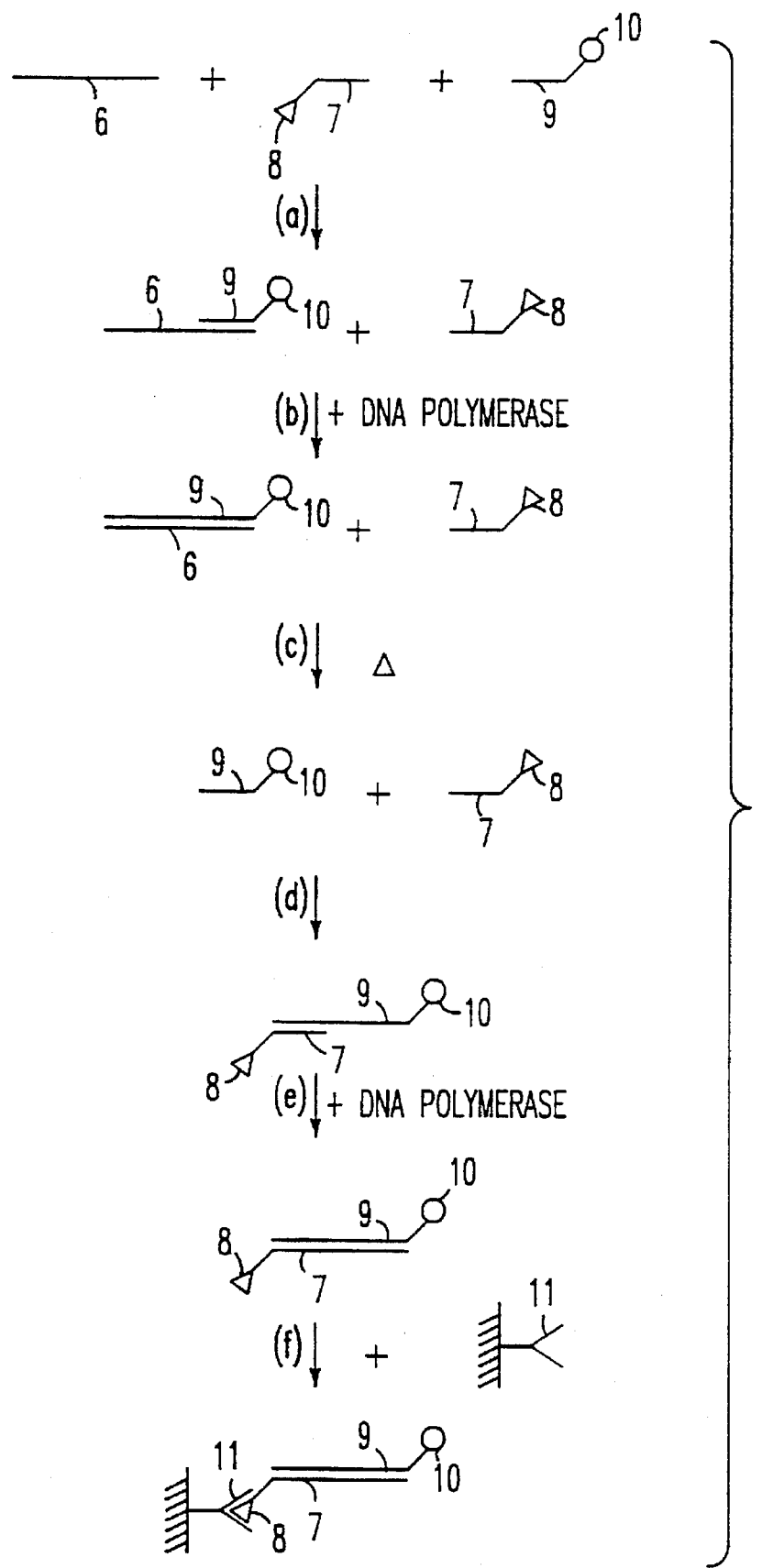
FIG. 3 schematically illustrates a DNA assay according to the present invention.

The present biomolecules bound to a colloidal metal particle are particularly useful for detecting the presence or absence of a target DNA in conjunction with PCR amplification. This type of assay is schematically illustrated in FIG. 3. A sample which may contain the target DNA (6) is incubated in steps (a) and (b) with: DNA polymerase, a DNA probe (7) which is identical to a portion of the target DNA (6) and which will be extended by the DNA polymerase and which is labelled with, e.g., biotin (8); and a DNA probe (9) which will hybridize with the target DNA (6) but not probe (7) and is labelled with a colloidal metal particle (10). After incubation and denaturation of the DNA, the single stranded DNA which contains probe (9) will then hybridize with probe (7) and incubation with DNA polymerase in step (e) will yield a double stranded DNA which contains both probe (7) and probe (9). The amplification may be extended by heating the double stranded DNA afforded by step (e) and again incubating in the presence of DNA polymerase. By maintaining an excess of probes (7) and (9) in the mixture, it is ensured that the double stranded DNA obtained will be labelled with both biotin (8) and the colloidal metal particle (10).

After the amplification is complete, the reaction mixture is contacted with immobilized streptavidin (11). Only if the target DNA (6) was present in the test sample will the reaction mixture contain double stranded DNA which contains both probe (7) and (9) and thus is labelled with both biotin (8) and colloidal metal particle (10). Thus, only if the target DNA (6) was present in the test sample will the colloidal metal particle (10) be bound to the immobilized streptavidin (11) and, thus, detected after washing. It is noteworthy that enzymes are not suitable as labels for such an assay because they will be denatured by the heating step required by PCR.

Of course, one of skill in the art will recognize that the above-described method may be carried out by using complementary binding systems other than the biotin-streptavidin system.

In the assays utilizing DNA or RNA labelled with a colloidal metal particle, the colloidal metal particle will typically be linked to the DNA or RNA by adsorbing avidin or streptavidin on the metal colloidal particle and allowing the avidin or streptavidin to bind to biotin which is covalently bonded to the DNA or RNA. The covalent binding of biotin to oligonucleotides is well known in the art and is described in: Chollet et al, *Nucleic Acids Res.*, vol. 13,
p. 1529 (185); Wachter et al, *Nucleic Acids Res.*, vol. 14, p. 7985 (1986); Agarawal et al, *Nucleic Acids Res.*, vol. 14, p. 6227 (1986); Urdea et al, *Nucleic Acids Res.*, vol. 16, p. 4937 (1988); Cook et al, *Nucleic Acids Res.*, vol. 16, p. 4077 (1988); Landergreu et al, *Science*, vol. 241, p. 1077 (1988); Mitchell et al, *Anal. Biochem.*, vol. 178, p. 239 (1989); Richterrich, *Nucleic Acids Res.*, vol. 17, p. 2181 (1989); Cocuzza, *Tetrahedron Letters*, vol. 30, pp. 2687–6290 (1989); U.S. Pat. No. 4,908,453; Alves et al, *Tetrahedron Letters*, vol. 30, pp. 3089–3092 (1989); U.S. Pat. No. 4,605,735; European Patent Application 202,758; Kempe et al, *Nucleic Acids Res.*, vol. 13, p. 45 (1985); U.S. Pat. No. 4,751,313; U.S. Pat. No. 4,711,955; and U.S. Pat. No. 5,128,476; all of which are incorporated herein by reference.

The presence of the biomolecule bound to the colloidal metal particle is detected by relying on the catalytic activity of the colloidal metal particle. The catalytic activity of the colloidal particle may be visualized by means of either a colorimetric (any change in absorbance of light) or chemiluminescent reaction. For example, the colloidal metal particle may be contacted with a mixture comprising $H_2O_2$ and a suitable hydrogen donor (HD) and the activity and, hence, amount of colloidal metal particle can be determined by measuring the amount of the reaction product, D, colorimetrically. Alternatively, the colloidal metal particle may be contacted with a mixture comprising a molecule which will react with a product catalytically produced by the colloidal particle to produce light. Examples of such chemiluminescent systems include the luminol system and the lucigenin system, which are explained in detail in the Examples below. Another suitable system is the oxalate ester system described in Beck et al, *Anal. Chem.*, vol. 62, pp. 2258–2270 (1990), which is incorporated herein by reference.

In another embodiment, the present invention relates to kits for carrying out an assay utilizing a biomolecule bonded to a catalytically active colloidal metal according to the present invention. Such kits will typically contain a first container containing a premeasured amount of a biomolecule bound to a colloidal metal. The kit may also contain a second container containing a premeasured and known amount of the target analyte to serve as a standard for the assay. The kit may further contain written instructions for carrying out the assay. The biomolecule bound to the colloidal metal may be contained in the kit in the form of a dry powder or a liquid suspension of known activity. If the biomolecule is contained in the kit in the form of a dry powder, then the kit may also contain measuring means for preparing a liquid suspension of known activity, such as a volumetric container.

Other features of the invention will become apparent in the course of the following descriptions of exemplary embodiments which are given for illustration of the invention and are not intended to be limiting thereof. For example, the present invention method need not include a step wherein the analyte-biomolecule-colloidal metal particle complex is separated from the sample.

EXAMPLES

I. Preparation of Colloids:

Example 1

To a 7 mL vial was added 2 mL of buffer, 5 μl of 8 wt. % platinum chloride in water solution (prepared from $H_2PtCl_6$, Pt content ~4 wt. %), 100 μl of reducing agent (37 wt. % formaldehyde, 25 wt. % glutaric dialdehyde or 10 mM ascorbic acid) and 10 μl of surfactant (1 mM). The vial was sealed and heated at approximately 75°–85° C. for 90 minutes in an oven. The vials were removed occasionally and color development noted. However, the reaction was not stopped when the first appearance of colloid was noted so that the particles could grow larger if the conditions were more optimal. The characterization of the particles is only qualitative. The size was judged by their tendency to settle. If complete settling had occurred, the particles were deemed to be large. If only limited settling had occurred after 24 hours, the particles were deemed to be small with precipitate. If no settling had occurred after 24 hours, the particles were deemed to be colloidal. From Table 1, it is evident that a large number of conditions generate colloidal particles.

Example 4

10 µl of a 8 wt. % platinum chloride solution in water (prepared from $H_2PtCl_6$, Pt content~4 wt. %) was added to 0.2M buffer. The solution was heated to approximately 90° C., and 100 µl of 37 wt. % formaldehyde was added. The heating was continued, and the solution was monitored for the appearance of colloidal platinum as evidenced by the formation of a brown color. Usually, precipitation of the colloid occurred.

Example 5—Mixed metals

10 µl of a 8 wt. % platinum chloride solution in water (prepared from $H_2PtCl_6$, Pt content~4 wt. %) and 50 µl of

TABLE 1

Reduction of Platinum Chloride Under Various Conditions and pHs

| | | \multicolumn{14}{c}{BUFFER} | | | | | | | | | | | | | |
|---|---|---|---|---|---|---|---|---|---|---|---|---|---|---|
| | | Phosphate | | | | Borate | | | Tris | | | Carbonate | | | |
| Reducing Agent | Surfactant | 7 | 8 | 9 | 10[a] | 8.6 | 9 | 10[a] | 7.2 | 8 | 9[a] | 8.3 | 9 | 10 | 11[a] |
| Ascorbate | None | O | S | S | O | B | S | S | C | C | C | O | O | N | N |
| | Cationic | L | S | S | O | B | S | S | C | C | C | O | O | N | N |
| | SDS | L | S | O | O | B | S | S | C | C | C | O | O | N | N |
| | Triton X100 | L | L | L | N | B | S | S | C | C | C | O | O | N | N |
| Formaldehyde | None | L | S | L | L | L | L | L | C | C | C | L | L | L | L |
| | Cationic | L | L | L | L | L | L | L | C | C | C | L | L | L | L |
| | SDS | S | S | L | S | L | L | L | C | C | C | L | L | L | L |
| | Triton X100 | S | L | L | L | L | L | L | C | C | C | L | L | L | L |
| Glutaric Dialdehyde | None | O | O | O | O | B | B | B | C | C | C | B | O | O | O |
| | Cationic | O | O | O | O | O | O | O | C | C | C | O | O | O | O |
| | SDS | O | O | O | O | O | O | O | C | C | C | O | O | O | O |
| | Triton X100 | O | O | O | O | O | O | O | C | C | C | O | O | O | O |

[a]The numbers under the Buffer is the pH.
Key:
Surfactants:
Cationic = Hexadecyltrimethylammonium bromide
SDS = Sodium dodecylsulfate
Results:
O = Colloid (Brown solution)
B = Colloid (Black solution)
S = Small Precipitates
L = Large Precipitates
N = No reaction and no color
C = Color but no reaction
H = Hazy solution

Example 2

300 mg of ascorbic acid and 300 mg of sodium bicarbonate were dissolved in 10 mL of distilled water. The solution was heated to approximately 90° C., and 100 µl of 8 wt. % platinum chloride solution in water (prepared from $H_2PtCl_6$, Pt content~4 wt. %) was added. The heating was continued for one hour during which time the solution became deep brown-yellow, which indicates a colloid. The dark solution sometimes had a small amount of platinum particles which appeared. These can be removed in subsequent steps. To be highly catalytic active, the colloid should be activated.

Example 3

10 µl of a 8 wt. % platinum chloride solution in water (prepared from $H_2PtCl_6$, Pt content~4 wt. %) was added to 0.2M buffer. The solution was heated to approximately 90° C., and 100 µl of 25 wt. % glutaric dialdehyde was added: The heating was continued, and the solution was monitored for the appearance of the colloidal platinum as evidenced by the formation of a brown color.

0.5 wt. % gold chloride was added to 0.2M buffer. The solution was heated to approximately 90° C., and 100 µl of 10 mM ascorbic acid was added. The heating was continued, and the solution was monitored for the appearance of colloidal platinum as evidenced by the formation of a brown color. Catalytic activity was similar to that observed with pure platinum.

II. Activation of particles:

The colloids prepared in the above-described manner should be removed from any excess reducing agent to enhance their catalytic activity. This may be accomplished by a number of means which include: dialysis, oxidation by hydrogen peroxide, column chromatography, and precipitation with washing. All these procedures produce colloidal particles with similar activities.

Activation by Hydrogen Peroxide

To the warm solution was added 1 mL of 30% hydrogen peroxide in 100 µl portions. Very rapid oxygen evolution was noted, as the platinum colloid is a very effective catalyst for the decomposition of hydrogen peroxide. The hydrogen peroxide removes some of the ascorbic acid and its decomposition products from the colloid surface and disperses the colloid if partial collagation has occurred. After this treatment, the colloid will readily coagulate unless a protective protein is added.

Activation by Dialysis

The protein to be coupled is added, and the solution is dialyzed against distilled water at 4° C. which removes more of the decomposition products of the ascorbic acid. Alternatively, the dialysis may be preformed first and then the hydrogen peroxide added followed by the protein. Either procedure gives comparable results, but the order may affect the activity of the protein in its intended usage, and the order selected would depend upon the protein.

Activation by Precipitation

3–5 Volumes of isopropanol or ethanol are added to the colloid, and the colloid is concentrated by centrifugation. The supernatant is discarded, and the colloid is resuspended in water. Without the isopropanol or ethanol, no precipitation occurs, unless the colloidal particles are large and black in color, which usually indicates coagulation of the colloids.

III. Attachment of Protein and Analysis

The protein is added to the solution of colloid and adsorbs non-specifically. Due to the small particle size of most preparations of the colloids, it has not been possible to clearly separate the colloidal particles from unadsorbed protein by either sizing columns, SDS gel electrophoresis, agarose gel electrophoresis, or HPLC sizing columns. Some separation occurs, but the degree of separation is frequently not sufficient to clearly separate the bound from unbound protein.

On horizontal, 1.5% Agarose gels, the colloid typically produces two bands. One broad smear moves faster than Bovine Serum Albumin (BSA) and indicates either highly charged particles or very small particles. The other band does not move at all and either indicates uncharged particles or very large particles. Upon mixing with BSA, these bands combine into one which moves slower than the original colloid and slightly faster than the unlabeled BSA. If insufficient protein is present to label all the colloidal platinum particles, then three bands containing platinum appear, two of which are unlabeled platinum. Similar patterns are observed on native, gradient polyacrylamide gels.

Some colloidal preparations appear to bind protein better than others as evidenced by the change in pattern on the Agarose gels. Both the ascorbate-reduced platinum and the glutaric dialdehyde-reduced platinum bind more protein than the formaldehyde reduced-colloid. However, the formaldehyde-reduced materials also coagulate and may not migrate due to the large size of the particles. The protein appears to be more stable on the glutaric dialdehyde-prepared colloids compared to the colloidal platinum prepared with the other reducing agents. However, the stability appears to be related to the storage buffer. Phosphate buffered saline (PBS) pH 7.0 appears to be optimum, whereas in borate pH 8.0, most immunological recognition capability is lost after 3 days at 5° C. The catalytic activity of the colloid is stable which indicates that the adsorbed antibody is being displaced by the buffer. Also, analysis by electrophoresis shows that the migration of particles with adsorbed proteins changes with time in some buffers probably due to aggregation.

Purification of Particles with Protein Prepared by the Ascorbate Method

After the adsorption of the protein, the excess protein is removed by chromatography on a Sephadex LH 150–120 prepared with phosphate buffered saline. The colloid elutes as a brown band and is well separated from any yellow decomposition products of the ascorbic acid not completely removed in the dialysis step. Likewise, any coagulated platinum will be retained at the top of the column. However, the protein, BSA, alkaline phosphatase or IgG elute just slightly slower than the colloid, and thus, the separation is not complete. This colloid appears to be slightly larger than most proteins in size (see below).

Sizing of the Particles

The colloid prepared in the above manner with ascorbate is between 20 nm and 100 nm in size as determined by it completely passing through a 100 nm Anotop membrane and being completely retained by a 20 nm Anotop membrane. The retained material may be removed from the membrane and employed in an immunoassay. This is an alternative method to using a sizing column for the removal of unbound protein.

The colloid prepared in the above manner with glutaric dialdehyde is less than 20 nm in size as determined by it completely passing through a 20 nm Anotop membrane with no loss in activity of UV-Visible absorption.

Various preparations were examined under an electron microscope. The particles were coagulated to varying degrees presumably due to the preparation conditions necessary for electron microscopy. It is unclear if these particles were coagulated in solution, because in all cases they readily passed through 100 nm filters but showed much greater aggregates under the electron microscope. In all cases, the particles composing the aggregates were less than 50 nm in diameter. The resolution of the electron microscope was insufficient to determine clearly the topography of the individual particles.

IV. Use in a dot ELISA:

Colloidal platinum was labeled with goat anti-biotin antibodies. Either Antibodies or BSA, the carrier protein, labeled with biotin were serially diluted in PBS and spotted onto nitrocellulose membranes. The remaining active sites were blocked with 1% BSA in PBS. The membranes were incubated with the colloidal platinum labelled with streptavidin for varying periods of time and with varying amounts of colloid. In the case of high amounts of carrier protein, a brown spot was barely visible where the biotinylated protein was applied. With lesser amounts of biotinylated protein, no spot was visible due to the color of the colloid. However, in all cases, when the nitrocellulose was placed in a solution of N,N-diethylphenylenediamine, 4-chloronapthol, and hydrogen peroxide, a strong blue precipitate appeared where the biotinylated protein had been applied. Also, the intensity decreased with decreasing amounts of biotinylated protein.

Colloidal platinum prepared with glutaric dialdehyde was labeled with strepavidin. The amount of strepavidin was optimized by both observing the pattern on Agarose gels and the sensitivity produced in a trial immunoassay. Either antibodies or BSA, the carrier protein, labeled with biotin were serially diluted in PBS and spotted onto nitrocellulose membranes. The remaining active sites were blocked with 1 wt. % BSA in PBS. The membranes were incubated with the labeled colloidal platinum for varying periods of time and with varying amounts of colloid. In the case of high amounts of carrier protein, a brown spot was barely visible where the biotinylated protein was applied. With lesser amounts of carrier protein, no spot was visible due to the color of the colloid. However, in all cases, when the nitrocellulose was placed in a solution of N,N-diethylphenylenediamine, 4-chloronapthol, and hydrogen peroxide, a strong blue precipitate appeared where the biotinylated protein had been applied. Also, the intensity decreased with decreasing amounts of biotinylated protein. Comparison with a commercial preparation of strepavidin-horseradish peroxidase conjugate incubated at the same time showed that the colloidal platinum was similar in sensitivity if not slightly better.

V. Optimization of catalytic activity:

The pH, buffer, and hydrogen peroxide concentration optimum is different for the catalytic platinum particles as compared to horseradish peroxide. Generally, much higher concentrations of peroxide are necessary to achieve rapid reaction, with the activity directly proportional to the hydrogen peroxide concentration. Likewise, the activity varies depending upon the buffer and substrate. A number of buffer systems, substrates and hydrogen peroxide concentrations were tested. The maximum hydrogen peroxide concentration used was 4 wt. %, although higher activity may be expected at higher concentrations. Two optimal systems are MBTH-DMAB in 0.1M phosphate buffer, pH 4 and N,N-diethylphenylenediamine-4-chloronapthol in 0.1M borate pH 7. The latter system produces a water-insoluble dye that localizes at the site of catalytic activity. The former system is for ELISA plate assays where a water-soluble dye is desirable.

VI. Detection by Chemiluminescence:

Lucigenin and luminol are dyes that may be used as the chemiluminescing material in two different systems. Reactions catalyzed by platinum can be easily detected by the luminol system (see Scheme 1). The reducing agent, hydrazine ($H_4N_2$), reacts with platinum to produce nitrogen ($N_2$) and hydrogen peroxide ($H_2O_2$). The $H_2O_2$ then oxidizes the luminol, producing light. The lucigenin system has a slightly different chemical pathway (see Scheme 2). The hydrazine reacts with the platinum and breaks down into nitrogen ($N_2$) and hydrogen ($H_2$). The $H_2$ activates the platinum, forming platinum hydride (Pt-$H_2$). The Pt-$H_2$ reduces the lucigenin to form a derivative. This derivative then reacts with oxygen and produces light. The formation of $H_2O_2$ as an intermediary product in the lucigenin system is not necessary.

Scheme 1

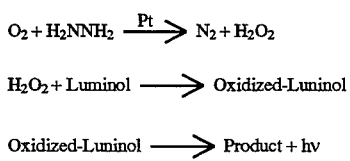

Scheme 2.

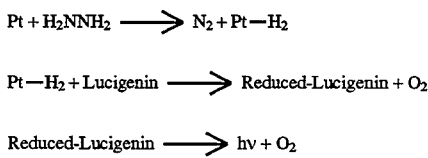

Materials and Procedures

The lucigenin reaction was tested on a spectrofluorometer with the light source off. The substrate contained a known amount of 0.2M buffer/ethanol solution, $4 \times 10^{-3}$M hydrazine, and $4 \times 10^{-4}$M lucigenin in a 2000 μl cuvette. Then 5 μl of platinum colloid was added and the emission intensity was measured per unit of time.

Different buffers were tested including borate, carbonate, and phosphate, of pH 8, 9 10, and 11. Various reducing agents were used other than hydrazine, for example sodium borohydride and formaldehyde.

The reactions were also assayed photographically. Trials were run in ELISA plates that had eight rows of twelve 2000 μl wells. The outside of the wells were sprayed with silver or black paint so that the light given off by one well would not stray to another well. 4×5 Instant Polaroid film was used for the photographs. The reagents in the reactions were varied as on the spectrofluorometer. The bottom two rows of each plate were left blank, for the control.

These reactions were also assayed on nitrocellulose strips about three centimeters in length and one centimeter in width. Several platinum colloid dilutions were made in small test tubes, starting with 1:100, 1:200, 1:400, 1:800, etc. 10 μl of BSA were added to each test tube to help the platinum stick to the nitrocellulose. 4 μl of each dilution were spotted onto the strips and were soaked in 0.4M borate buffer pH 8. A hole was drilled in the center of a 60 mm petri dish. The open end of the dish was covered with plastic wrap, which was held onto the plate with a rubber band. The strip and substrate were put into the hole and exposed on the film through the plastic wrap (this allowed closer contact with the film and sharper images than obtained through a thick plastic plate) for a specific length of time.

After the pictures were taken, the strips were developed colormetrically. The substrate for the color system contained ethanol, 4-chloro-1-naphthol, N,N-diethylphenylenediamine dihydrochloride, 0.4M borate buffer pH 8, and $H_2O_2$. The intensity/density of the blue-colored spots showed the amount of platinum present. Comparisons were made between the color and the light system to determine how well the chemiluminescence worked. Both methods gave sensitive readings of the amount of platinum colloid present.

The luminol system was also tested on a spectrofluorometer. Known volumes of 0.2M borate buffer, $4 \times 10^{-3}$M hydrazine, 5 mg/ml luminol, and 10 mg/ml hematin were mixed together.

With the lucigenin system, improvements were made so that the emission of light was more intense and long-lasting. 5 μl of $2 \times 10^{-3}$M Pt added to 950 μl of a 0.2M borate pH 9.5 buffer, 950 μl of ethanol, 100 μl of hydrazine, and 10 μl of lucigenin in a 2000 μl cuvette yielded the best results on the spectrofluorometer. Generally, the phosphate buffer gave a light intensity that was much too low and the carbonate buffer gave a high background reading. There were problems with keeping the background low because when the pH was increased, the light emission went up, but unfortunately, so did the background. Similar problems were encountered when adding a greater volume of lucigenin to the cuvette.

The lucigenin reaction gave off a large amount of light, but the intensity fell rapidly with time. It was difficult to determine why the light intensity dropped so fast. One possibility was that some component of the reaction was being consumed. The order in which the reagents were added was tested to see if that would affect the total chemiluminescence intensity. When the hydrazine was added last, the luminescence was about half the intensity of when the platinum or the lucigenin was added last. This implied that for some reason, the lucigenin was being consumed. Further investigation is being done to find a solution to this problem.

When the lucigenin system was tested on the nitrocellulose, a slightly different combination of reagents gave the clearest light emission. A solution containing 2 ml of 0.2M borate pH 9.5 buffer, 2 ml of ethanol, 500 μl of hydrazine, 10 μl of lucigenin, and a small spatula scoop of tetrabutylammonium bromide worked the best. The tetrabutylammonium bromide seemed to reduce the background light significantly because it reduced the non-specific adsoption of the lucigenin and the acridone to the nitrocellose. The smallest amount of platinum that was detectable was about 300 picograms.

The lucigenin system was also tested on the spectrofluorometer. Pilipenko et al disclose a system containing $1\times10^{-4}$M lucigenin, 0.02M $H_4N_2$, sodium hydroxide (NaOH) at pH 13, and platinum concentrations of $1\times10^{-3}$ to $1\times10^{-2}$ (*J. Analytical Chem. USSR*, vol. 28, pp. 1004–8 (1971)).

The concentration of platinum used was $2\times10^{-3}$M Pt. The light produced using the reported system was useless, because the background noise almost equaled the light intensity. With such a high background, it was impossible to test this reaction photographically because the light emission could not be discerned from the background.

The lucigenin reaction gave a peak signal/background of 43,000/30 or 12,000:1 and fell off over a period of thirty minutes. Although the background increased with time, it remained well below 30 units. These results were much better, because with such a low background noise level, the light emission could be photographed successfully.

The luminol system was also tested with the spectrofluorometer. At a 0.2M borate pH 11 buffer, the light intensity continued to rise, even after thirty minutes. However, results on the nitrocellulose strips were not as good.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for detecting an analyte in a sample, comprising:
   (i) contacting a sample, which may contain an analyte, with a biomolecule which is bonded to a catalytically active colloidal metal particle through a polymer or copolymer partially coating said catalytically active colloidal metal particle, or through both a polymer or copolymer partially coating said catalytically active colloidal metal particle and a catalytically active colloidal metal particle, said biomolecule being a specific binding complement of said analyte, to obtain an analyte-biomolecule-colloidal metal particle complex;
   (ii) contacting said analyte-biomolecule-colloidal metal particle complex with a substrate which forms a product in a reaction catalyzed by the colloidal metal particle of said complex; and
   (iii) detecting said analyte-biomolecule-colloidal metal particle complex by detecting said product produced by a reaction of said substrate by the colloidal metal particle of said complex to indicate the presence or absence of said analyte in the sample,
   wherein said colloidal metal particle comprises a metal selected from the group consisting of Ni, Fe, Pt, Pd, Ag, and mixtures and alloys thereof; and said biomolecule is selected from the group consisting of antibodies, antigens, avidin, streptavidin, biotin, proteins bonded to a hapten, and nucleic acids.

2. The method of claim 1, wherein said colloid metal particle comprises a metal selected from the group consisting of platinum, palladium, and silver.

3. The method of claim 1, wherein said biomolecule is a peptide.

4. The method of claim 3, wherein said polypeptide is selected from the group consisting of antibodies, avidin and streptavidin.

5. The method of claim 1, wherein said colloidal metal particle has a greatest dimension less than 50 nm and a smallest dimension greater than 1 nm.

6. The method of claim 1, wherein said detecting is carried out by colorimetrically measuring an amount of a product catalytically produced by said colloidal metal particle.

7. The method of claim 1, wherein said detecting is carried out by measuring light produced by a chemiluminescent compound which is produced by reaction of a precursor to the chemiluminescent product and a product catalytically produced by the colloidal metal particle.

8. The method of claim 1, which is a competitive assay.

9. The method of claim 1, which is a sandwich assay.

10. The method of claim 1, wherein said catalytically active colloidal metal particle comprises an alloy selected from the group consisting of platinum-gold alloys and platinum-palladium alloys.

11. A kit, comprising:
   (a) a first container means containing a known amount of a biomolecule bonded to a catalytically active colloidal metal particle; and
   (b) a second container means containing reagents which will yield a colored product or produce light, in a reaction being catalyzed by said colloidal metal particle,
   wherein said catalytically active colloidal metal particle comprises a metal selected from the group consisting of Ni, Fe, Pt, Pd, Ag, and mixtures and alloys thereof.

12. The kit of claim 11, wherein said colloidal metal particle comprises a metal selected from the group consisting of platinum, palladium, and silver.

13. The kit of claim 11, wherein said biomolecule is selected from the group consisting of antibodies, avidin, streptavidin, proteins covalently bound to biotin, and proteins covalently bound to a hapten or antigen.

14. The kit of claim 11, wherein said colloidal metal particle has a greatest dimension less than 50 nm and a smallest dimension greater than 1 nm.

15. The kit of claim 11, further comprising written instructions for carrying out an assay.

16. The kit of claim 11, further comprising a third container means containing a known amount of an analyte, which is a binding complement of said biomolecule.

17. The kit of claim 11, wherein said catalytically active colloidal metal particle is partially coated with a polymer or copolymer.

18. The kit of claim 11, wherein said catalytically active colloidal metal particle comprises an alloy selected from the group consisting of platinum-gold alloys and platinum-palladium alloys.

* * * * *

UNITED STATES PATENT AND TRADEMARK OFFICE
CERTIFICATE OF CORRECTION

PATENT NO.   :   5,637,508
DATED:       :   June 10, 1997
INVENTOR(S)  :   David A. KIDWELL et al It is certified that error appears in the above-identified patent and that said Letters patent is hereby corrected as shown below:

Column 18, line 7, change "peptide" to --polypeptide--.

Signed and Sealed this

Fourteenth Day of July, 1998

Attest:

BRUCE LEHMAN

*Attesting Officer*    *Commissioner of Patents and Trademarks*